United States Patent [19]
King et al.

[11] Patent Number: 5,301,012
[45] Date of Patent: Apr. 5, 1994

[54] OPTICAL TECHNIQUE FOR RAPID INSPECTION OF VIA UNDERETCH AND CONTAMINATION

[75] Inventors: Mark R. King, Milton, N.Y.; Wendell B. Scism, Boise, Id.

[73] Assignee: International Business Machines Corporation, Armonk, N.Y.

[21] Appl. No.: 968,733

[22] Filed: Oct. 30, 1992

[51] Int. Cl.$^5$ .............................. G01N 21/88
[52] U.S. Cl. ..................... 356/398; 356/237
[58] Field of Search ............ 356/398, 394, 237, 372, 356/429–431

[56] References Cited

U.S. PATENT DOCUMENTS

| | | | |
|---|---|---|---|
| 3,448,280 | 6/1969 | Blitchington, Jr. et al. | 250/559 |
| 4,040,745 | 8/1977 | Belleson . | |
| 4,088,312 | 5/1978 | Froach et al. | 269/21 |
| 4,386,707 | 6/1983 | Stube | 209/564 |
| 4,464,050 | 8/1984 | Kato et al. | 356/237 |
| 4,560,273 | 12/1985 | Ando et al. | 356/237 |
| 4,630,276 | 12/1986 | Moran | 372/15 |
| 4,656,791 | 4/1987 | Herrington et al. | 51/410 |
| 4,669,875 | 6/1987 | Shiba et al. | 356/237 |
| 4,684,113 | 8/1987 | Douglas et al. | 269/21 |
| 4,811,410 | 3/1989 | Amir et al. | 382/8 |
| 4,841,242 | 6/1989 | Brunner | 324/158 R |
| 4,843,329 | 6/1989 | Beha et al. | 324/73 PC |
| 4,868,492 | 9/1989 | Beha et al. | 324/73 PC |
| 4,894,790 | 1/1990 | Yotsuya et al. | 364/552 |
| 4,999,510 | 3/1991 | Hayano et al. | 250/571 |

FOREIGN PATENT DOCUMENTS 60-57241 4/1985 Japan .
63270204 5/1990 Japan .

OTHER PUBLICATIONS

IBM Technical Disclosure Bulletin, vol. 16, No. 9, Feb. 1974, pp. 2826 to 2828; "Scanner for Opaque Samples", by L. P. Hayes.
IBM Technical Disclosure Bulletin, vol. 30, No. 11, Apr. 1988, pp. 242 & 243; "Laser Scan System for Surface Inspection", by D. Wagner.

Primary Examiner—F. L. Evans
Attorney, Agent, or Firm—Whitham & Marhoefer

[57] ABSTRACT

Sensitivity and resolution of an automated inspection system are improved and data processing loads for defect detection are reduced, increasing inspection speed, by fully illuminating an area corresponding to a nominal feature shape formed on a surface. Scanning of the illuminated area thus provides resolution of defects far smaller than the area of the illuminated spot. A preferred application of this automated inspection system is for the high speed screening of lamina or substrates having a pattern of through-holes formed therein, particularly for the formation of via connections therein. Screening for insufficient clear area of through-holes is done simply by applying a threshold to the output representing the amount of illumination transmitted and preferably reflected through the through-hole.

16 Claims, 2 Drawing Sheets

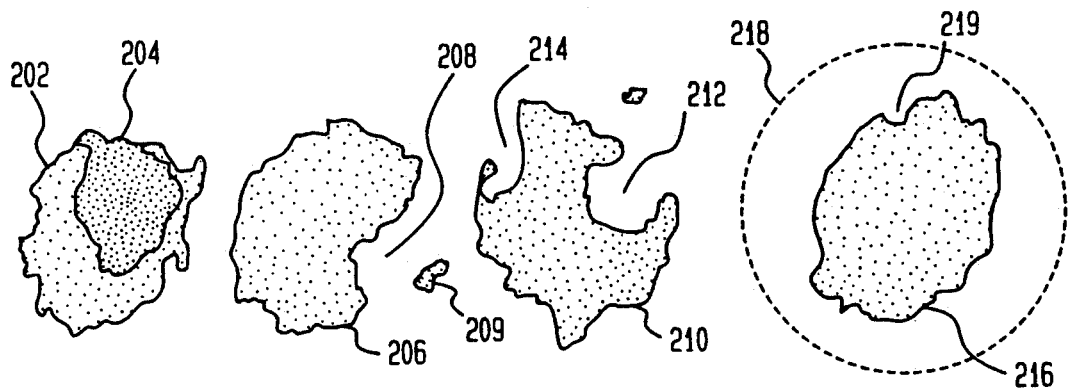
FIG. 2A  FIG. 2B  FIG. 2C  FIG. 2D
FIG. 3
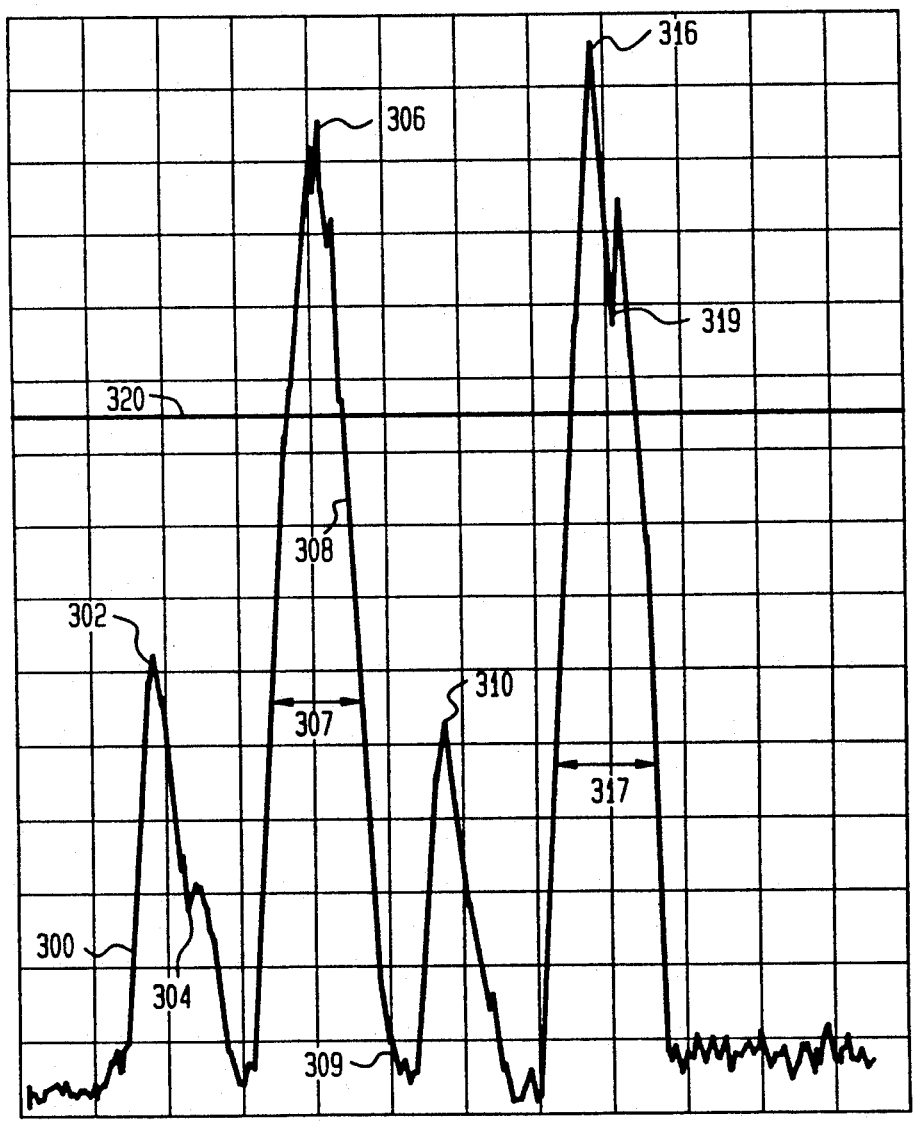

OPTICAL TECHNIQUE FOR RAPID INSPECTION OF VIA UNDERETCH AND CONTAMINATION

BACKGROUND OF THE INVENTION

1. Field of the Invention

The present invention generally relates to optical monitoring of manufacturing processes and, more particularly, to the optical inspection of apertures in a substrate or lamina.

2. Description of the Prior Art

In order to obtain good quality during the course of a manufacturing process, it is a generally accepted practice to inspect the results of most, if not all, operations. Such inspections are particularly necessary where automated equipment is used to perform the process. If an operation is carried out improperly, causing defects in the workpiece which cannot be remedied, further operations on the defective workpiece can be avoided. If the defect can be remedied, appropriate action can be taken at the most advantageous point during the further manufacturing operations.

Such inspections are particularly necessary where automated equipment is used to perform the process. Inspection of the workpiece after an operation is carried out can also reveal much important information concerning the operating condition of the automated apparatus such as wear, alignment and other adjustments.

Recent designs of electronic components are generally characterized by the small feature size of patterns which may form or interconnect many different elements of the electronic component although many features of the pattern may be formed during a single manufacturing operation. Due to the large numbers of features which may result from a single manufacturing operation, automated inspection systems have been developed to reduce inspection times. Exemplary automated inspection systems are discussed in U.S. Pat. Nos. 4,040,745 to J. G. Belleson and 4,464,050 to K. Kato et al. Other exemplary arrangements are disclosed by L. P. Hayes in "Scanner for Opaque Samples", IBM Tech. Discl. Bull. Volume 16, No. 7, (February, 1972), and "Laser Scan System for Surface Inspection", IBM Tech. Discl. Bull. Vol. 30, No. 11 (April, 1988).

Virtually all such inspection systems relying on reflection of radiation from a surface share the common features of a source of radiation, a means for focussing that radiation on an inspection spot and a detector for radiation transmitted through or reflected by the sample. Such systems may include other optical elements such as filters to improve the signal to noise ratio of the observation or elements such as mirrors or beam splitters to provide scanning or to improve the measurement geometry of the system.

However, it is well-accepted that the resolution of such systems is limited by the size of the focussed spot of radiation. That is, a defect which is smaller than the area of the focussed spot will cause only a small difference in reflection or transmission and may not be detected. U.S. Pat. No. 4,999,510 to F. Hayano et al varies the beam size to discriminate foreign particles of different sizes. Further, in manufacturing processes where features are formed on a surface, such as through-holes, generally referred to as vias (particularly when filled with a conductive material), in an insulating lamina or substrate, an improperly formed or missing feature may have similar reflectance to the surrounding surface. It is also likely that the size of a defect in a feature will be smaller than the feature itself. Therefore, expensive and complex optical systems have been employed to reduce the size of the illuminated radiation spot in order to improve resolution of optical inspection systems.

Increases in resolution of the inspection systems present additional problems since it results in additional data to be processed. The data processing for feature extraction is computationally intensive and the finer segmentation of the image in accordance with finer resolution increases the data to be processed by the square of the increase in linear resolution (e.g. lines per mm.). Therefore, as the trend in electronic circuit modules has increased and minimum feature size has decreased, dictating finer resolution from automated inspection systems, the computational loads required for analysis of the inspection data has limited throughput of the manufacturing processes as well as greatly increased the expense of the inspection systems. The limitation of the manufacturing processes also increases the cost of the components manufactured.

SUMMARY OF THE INVENTION

It is therefore an object of the present invention to provide a surface inspection system which reduces or avoids segmentation of the field of view and presents data in a form which can be rapidly and simply processed to determine the presence of defects in that surface.

It is another object of the present invention to provide a surface inspection system in which the extraction of feature defects is simplified.

It is a further object of the present invention to provide an automated inspection system capable of inspection of apertures in a lamina or substrate at high speed.

In order to accomplish these and other objects of the invention, an apparatus and method of automated inspection are provided including the steps of illuminating an area of a surface corresponding to the area of a feature formed thereon to form an illuminated area, scanning the illuminated area over the surface and detecting characteristics of the amount of said illumination transmitted through or reflected from the surface or means for performing the same.

BRIEF DESCRIPTION OF THE DRAWINGS

The foregoing and other objects, aspects and advantages will be better understood from the following detailed description of a preferred embodiment of the invention with reference to the drawings, in which:

FIGS. 2A, 2B, 2C and 2D depict the profiles of actual defects detected by the inspection system in accordance with the present invention, and FIG. 3 graphically depicts the output of the inspection system in accordance with the invention for defects illustrated in FIGS. 2A-2D.

DETAILED DESCRIPTION OF A PREFERRED EMBODIMENT OF THE INVENTION

Figure 1:
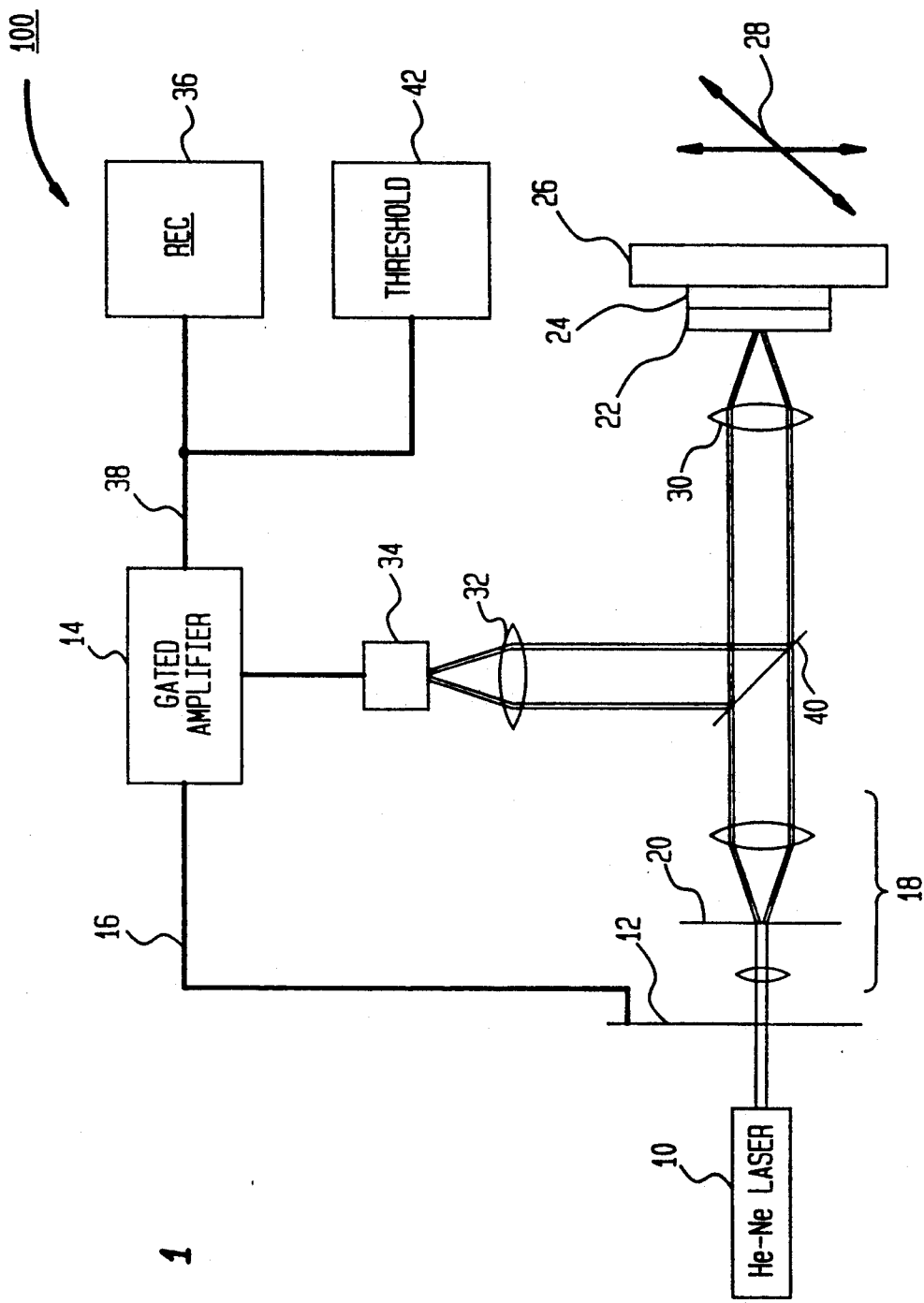
FIG. 1 is a schematic view of a preferred form of the defect detection system in accordance with the present invention.

Referring now to the drawings, and more particularly to FIG. 1, there is schematically shown a preferred form of the inspection system 100 in accordance with the invention. The illumination source 10 is preferably a He-Ne Laser, the output of which is timed by a chopper 12 which is synchronized with gated lock-in amplifier 14 over connection 16. This synchronization permits substantial increase in the signal to noise ratio of the measurement due to ambient light conditions. The lock-in amplifier provides a continuous output of the amplitude of the signal at the chopper speed (e.g. approximately 1 KHz). The chopped laser illumination is then passed through a collimator arrangement 18, the details of which are unimportant to the invention except that it preferably includes an aperture plate 20 which defines an image spot size at the sample. The collimator should also provide a substantially constant illumination profile over the entire spot area.

This image spot is then focussed on sample 22 by projection lens 30. Sample 22 is preferably positioned in front of a highly reflective surface 24 on a translation table 26 capable of moving the sample 22 by precise amounts in, for example, orthogonal directions as indicated by arrows 28. Light reflected from the sample 22 or surface 24 (at the locations of vias in sample 22) is reflected back, preferably along the original beam path in order to keep the optical properties of the system precisely constant, to a partial reflector or beam splitter 40. The returned beam is then focussed on a photodetector 34 by focussing lens 32. The photodetector 34 is preferably a photodiode but other devices such as photomultiplier tubes could also be effectively used. The output of photodetector 34 is gated in synchronism with chopper 12 and amplified and the output 38 thereof is recorded by recorder 36 or other desired data storage, retrieval and processing device such as a threshold discriminator 42.

It is very important to an understanding of the invention to recognize that the optical system of the present invention, while appearing superficially similar to the optical systems of known automated inspection devices, is specific to detection of a particular type of surface defect. Therefore, a brief discussion of a preferred application of the invention will be provided.

Preferred constructions of electronic devices and components have often included an insulating lamina or substrate having conductive patterns thereon. Printed circuits are well known examples of such constructions. Recently, electronic components have been constructed as multi-layer modules (MLM) having a plurality of lamina with a conductive pattern applied to each such lamina. These lamina are laminated together to form a unitary structure which may provide upwards of two million separate connections between the terminals of integrated circuits mounted thereon. These numerous connections have a three-dimensional configuration and connections between various layers of the MLM component are formed by filling through-holes or vias in the respective lamina.

To obtain high pattern density, particularly in so-called distribution wiring layers for making connections to individual integrated circuit chips, the vias must be very small and precisely located. A typical via diameter is nominally about 80 $\mu$m. The pitch or separation of these vias or through-holes in a particular pattern is often on the order of about 150 $\mu$m to 500 $\mu$m and the diameter of the via holes may not be significantly increased without removing a substantial portion of the material of the lamina and making them too fragile to handle during manufacturing processes.

Accordingly, laser ablation is the technique of choice for forming the through-holes which will be filled to form vias. While other processes may be used, such other processes are generally susceptible to the same defects as will be discussed in connection with laser ablation. Any material removal process such as laser ablation may cause defects in holes by incomplete material removal or contamination of the surface with the material removed. Since the formation of through-holes in insulative lamina is ultimately for the purpose of conductor formation, such incomplete material removal or contamination with insulative material may cause defective conductor formation. That is, when the conductors are formed by filling of the holes with conductive material, a high resistance or open may result if the hole is partially filled, contaminated or otherwise improperly formed. High resistance connections will often open after the component has been placed in service due to excessive heat generated by the high resistance.

Therefore, to rapidly screen a surface having a large plurality of through-holes, the invention provides that the optical system develop an illumination spot larger than the nominal area of a through-hole but smaller than the separation between through-holes so that an entire hole area can be simultaneously illuminated. The sample is continuously or incrementally moved through a scanning pattern and hole location can be monitored by the position of the sample at the time a hole is detected. Hole defects which are smaller than the hole can be resolved by a combination of amplitude of reflected radiation and sample position. Sensitivity of the system is preferably increased by passing the illumination through the hole twice by reflection from surface 24. Thus attenuation of the illumination due to defects will be increased and discrimination of defects from the resulting data made less critical and more reliable.

It should be noted in this regard that positional variation of hole locations affects the quality of the lamina much in the same way as incomplete material removal since errors of registration reduce the contact area or conductive cross-section of vias from lamina to lamina just as improper hole formation or contamination reduces the conductor cross-section within the lamina. Therefore, it is sufficient for all defects of interest to be able to observe the position of the maximum area and to have a measure of that area. The development of an illumination spot slightly larger than a nominal area of a through-hole together with continuous or incremental scanning over intervals which are small in comparison to the pitch of the hole pattern is specific to this information. Therefore no excess data is collected which must be processed to extract information which may represent defects.

Referring now to FIGS. 2A–2D and FIG. 3, the operation of the inspection system in accordance with the invention will now be described. FIGS. 2A–2D, while presented as separate Figures for ease of reference, represent actual microscopic views of the interiors of through-holes at via sites which are nominally of 80 $\mu$m diameter and evenly spaced on a lamina or substrate. FIG. 2A represents a substantially fully formed through-hole 202 which has been contaminated by a foreign particle 204. FIG. 2B represents an imperfectly formed through-hole 206 (including area 209) due to the presence of substrate or lamina material at 208. The material at 208 represents material which may or may not be detached from the lamina or substrate but which remains in the through-hole 206. FIG. 2C represents a defective through-hole 210 where substantial substrate or lamina material remains at locations 212 and 214. FIG. 2D represents a substantially perfect through-hole 216 although it is slightly out of round and exhibits irregularities 219. The preferred approximate size of the illumination spot is shown by dashed line 218 in FIG. 2D for purposes of comparison.

The result of scanning these four through-holes of FIGS. 2A-2D on the same substrate is shown in FIG. 3. The curve 300 showing the amount of reflected light clearly reveals and substantially categorizes the defects represented in FIGS. 2A-2D. Specifically, the reduced height of peak 302 indicates that the area of the through-hole is significantly obstructed. The existence of trough 304 generally indicates a material other than the substrate material and the position of the trough indicates the position of the particle somewhat to the right of the hole (in the scanning direction). The height of peak 306 indicates that some reduction of area of through-hole 206 is present but that the clear area of the hole is sufficient for reliable via production. The steeper slope at 308 to the right of peak 306 indicates the position of partial obstruction 208 but the centroid of the hole area is not affected to a degree which would compromise registration, as indicated by the position of peak 306. The toe 309 of the peak 306 reveals the small hole feature 209 in FIG. 2B. The reduced height of peak 310 indicates defective formation of through-hole 210 and the leftward shift of the peak indicated that the major portion of material 212 remaining in the through-hole is to the right. The height of peak 316 indicates that hole 216 is substantially perfect. Even in this case, however, the eccentricity of the through-hole 216 is reflected in the narrow width of the collective peak 316, 319 at 317 as compared to the width 307 of peak 306. Even some of the irregularities (e.g. 219) of the perimeter of through-hole 216 are reflected by trough 319.

While it is thus seen that many features may be resolved which are much smaller than the optical illumination spot, by virtue of the extreme sensitivity of the invention to the particular defects of interest, it is important to note that the output curve 300 reflects the cross-sectional area of each via hole which is available for via formation. Accordingly, screening the lamina for through-hole defects need not include any processing of data beyond mere thresholding at a predetermined level such as 320. This minimal processing can easily be done synchronously with scanning and at the highest scanning rate obtainable from translation table 26. Information affecting registration could be easily obtained as well by mere detection of locations of peaks. While via location may not vary sufficiently in lamina with no through-hole defects, an offset to obtain a best fit of via locations could be easily obtained by averaging of peak location variation, if desired.

In view of the foregoing, it is seen that the invention provides a high speed automated inspection systems for defects in the formation of through-holes in a substrate or lamina and representing a large amount of information in relatively little data and in a form which can be rapidly and easily processed. It should be noted that the efficacy and sensitivity of this process results, in large degree, from the approximate congruence of the illuminated spot and feature within which defects are to be resolved and which provides spatial filtering specific to the feature to be inspected. Therefore the illuminated spot need not be circular but should conform generally to the nominal shape of the feature to be inspected. The invention should therefore be understood to include non-circular feature shapes such as rectangles which could be used as connection pads. Similarly, the invention is not limited to the inspection of through-holes but is applicable to any type of surface feature which will provide significant reflective or transmissive contrast. In this regard, it should be noted that contrast can often be enhanced by the spectral content of the illuminating radiation over a wide range of wavelengths (e.g. from far infrared to far beyond ultraviolet wavelengths). Thus the invention should not be considered as limited to light in the visible spectrum.

While the invention has been described in terms of a single preferred embodiment, those skilled in the art will recognize that the invention can be practiced with modification within the spirit and scope of the appended claims.

Having thus described out invention, what we claim as new and desire to secure by Letters Patent is as follows:

1. A method of inspecting features of a surface of an object comprising the steps of
    illuminating an area of said surface corresponding to an area of a feature formed thereon to form an illuminated area by projecting radiation along a beam path,
    scanning said illuminated area over said surface, and
    detecting characteristics of the amount of said illumination transmitted through or reflected from said object along said beam path.

2. A method as recited in claim 1, wherein said illuminated area is approximately congruent with a nominal shape of said feature.

3. A method as recited in claim 1, wherein said detecting step includes the step of discriminating said amount of transmitted or reflected illumination at a predetermined threshold.

4. Automatic inspection apparatus including
    means for illuminating an area of an object corresponding to a feature formed on a surface thereof to form an illuminated area by projecting radiation along a beam path,
    means for scanning said illuminated area over said object, and
    means for detecting characteristics of the amount of illumination of said illuminated area transmitted through or reflected from said object along said beam path.

5. Automated inspection apparatus as recited in claim 4, wherein said means for illuminating an area comprises an aperture defining the shape and size of said illuminated area.

6. Automated inspection apparatus as recited in claim 5, wherein said shape of said aperture corresponds to a shape of said feature.

7. Automated inspection apparatus as recited in claim 4, wherein said means for illuminating comprises a laser radiation source.

8. Automated inspection apparatus as recited in claim 4, wherein said means for scanning includes a translation table.

9. Automated inspection apparatus as recited in claim 8, wherein said translation table can provide continuous movement.

10. Automated inspection apparatus as recited in claim 8, wherein said translation table can provide incremental movement.

11. Automated inspection apparatus as recited in claim 10, wherein an increment of said incremental movement is less than a nominal transverse dimension of said feature.

12. Automated inspection apparatus as recited in claim 4, wherein said means for detecting comprises threshold detection means.

13. Automated inspection apparatus as recited in claim 4, wherein said means for detecting comprises a recording means.

14. Automated inspection apparatus as recited in claim 4, wherein said means for detecting comprises a photodiode.

15. Automated inspection apparatus as recited in claim 4, wherein said means for detecting comprises a gated amplifier and said means for illuminating comprises a chopper.

16. Automated inspection apparatus as recited in claim 15, wherein said means for detecting comprises a photodiode.

* * * * *